United States Patent [19]

Butler

[11] 4,150,593

[45] Apr. 24, 1979

[54] RETRACTABLE SPECIMEN HOLDER FOR A ROTARY MICROTOME

[76] Inventor: James K. Butler, 1412 Woodbine Ct., Arlington, Tex. 76012

[21] Appl. No.: 898,940

[22] Filed: Apr. 21, 1978

[51] Int. Cl.² ............................................. G01N 1/06
[52] U.S. Cl. ......................................... 83/42; 83/412; 83/718; 83/915.5
[58] Field of Search .............. 83/718, 720, 721, 915.5, 83/42

[56] References Cited

U.S. PATENT DOCUMENTS

| | | |
|---|---|---|
| 3,077,806 | 2/1963 | Hellstrom ........................ 83/915.5 X |
| 3,691,889 | 9/1972 | Forsstrom ........................ 83/915.5 X |
| 3,733,948 | 5/1973 | Pickett ............................. 83/915.5 X |
| 3,771,405 | 11/1973 | Blum ............................... 83/915.5 X |
| 4,126,069 | 11/1978 | Shimonaka ...................... 83/915.5 X |

FOREIGN PATENT DOCUMENTS 844260 8/1960 United Kingdom .................... 83/915.5

*Primary Examiner*—J. M. Meister

*Attorney, Agent, or Firm*—Charles W. McHugh

[57] ABSTRACT

An apparatus for selective attachment to a rotary microtome in order to permit separation of the specimen from a cutting knife during the return stroke of the specimen. A small frame is adapted to fit within the conventional specimen holder or chuck of the microtome; and the frame carries a solenoid with a movable core. Attached to the forward end of the movable core is an auxiliary specimen holder; attached to the other end of the core is a plate against which a compression spring constantly presses. The preferred power supply for the solenoid is a filtered 30 volt DC power supply. The solenoid is energized only during the downward, cutting stroke of the microtome, and it is de-energized before the arm starts its return stroke. The spring urges the specimen holder away from the knife when the solenoid is de-energized. The apparatus may be readily installed on any conventional rotary microtome with minimal skilled labor; and it may be removed at will to restore the microtome to its original condition.

22 Claims, 4 Drawing Figures

RETRACTABLE SPECIMEN HOLDER FOR A ROTARY MICROTOME

This invention relates generally to microtomes of the type commonly referred to as rotary microtomes; more particularly, it relates to an appendage for providing return stroke separation of a specimen with respect to a cutting knife.

In the prior art, it is well known to effect separation of a specimen block from a cutting knife when the specimen is being returned to an upper position in preparation for a fresh cutting stroke. However, the mechanism for reliably accomplishing such retraction of the specimen holder has usually been somewhat complex, and only relatively expensive microtomes normally have this desirable capability. Because of the complexity of a typical return stroke mechanism, and the need to maintain a high degree of rigidity in specimen support, the only known retraction devices have been those which were built into microtomes as an integral part of their supporting structure. That is, it is believed that there has never been an add-on device which offers the advantage of controlled specimen/knife separation while maintaining the rigidty that is necessary for accurate work. Accordingly, it is an object of this invention to provide an apparatus which can be selectively attached to a rotary microtome for effecting return stroke separation.

Before proceeding with a detailed description, perhaps it would be appropriate to first describe the problem which is addressed by this invention. With a conventional rotary microtome (also sometimes referred to as a paraffin microtome), the action of the specimen support arm typically produces what is referred to as "scrubbing" on the return or upward stroke. Scrubbing occurs because the specimen follows exactly the same path in moving upward as it traveled on its downward, cutting stroke. The potential for scrubbing has always existed in non-retracting microtomes; but, as long as relatively firm paraffin was used as the supporting medium for tissue samples, the lack of resiliency in the paraffin minimized the problem. In recent years, however, there has been a trend to use other supporting materials, such as water-soluble glycol methacrylate. Among the advantages of using water-soluble materials are better tissue preservation (because no heating is required) and the opportunity of obtaining thinner tissue slices. The major disadvantage of a plastic such as glycol methacrylate is its resiliency, because the knife will slightly compress the specimen block during a downward stroke. Then, as the specimen block passes below the knife edge and the cutting force is released, the resiliency in the plastic causes it to spring forward for a small distance, so that it actually projects slightly beyond the cutting plane. Upward travel of the specimen block along the original travel path subsequently causes the specimen to impinge upon the knife face in such a way that the specimen must be deformed in order to move past the knife. Therefore, the situation is that there are literally thousands of rotary microtomes which have been manufactured and sold over the past several years, back when paraffin specimens were perhaps the only specimens which were made. And, now that people are wanting to change to water-soluble plastics, there is almost a necessity that they have more sophisticated equipment—which has a retraction capability—in order to avoid the scrubbing phenomenon.

As one way of avoiding the abandonment of a great amount of valuable equipment, it is an object of this invention to permit the upgrading of all of these old rotary microtomes with a modification kit which can produce the same kind of specimen motions that are currently possible only in competitive microtomes costing two or three times as much as rotary microtomes.

Another object is to provide an appendage which can be installed on existing microtomes with a minimal amount of skilled labor.

A further object is to provide a specimen retraction capability in microtomes which were not originally designed to produce that action—but without interfering with the original reciprocating and indexing mechanisms of the microtomes.

These and other objects will be apparent from a careful study of the specification and the claims appended thereto, as well as reference to the accompanying drawings in which:

In brief, the invention includes a frame having an external configuration which is adapted to be selectively fixed fo the reciprocating mechanism of a conventional microtome. Preferably, the frame is small enough to fit within the original chuck, or at least the specimen chuck holder. A solenoid is mounted within said frame, and it includes a coil, a movable core, a plate affixed to the rearward end of said movable core, and an auxiliary specimen holder fixed to the forward end of the movable core. A spring constantly urges the plate and the movable core rearwardly away from the coil. Electrical circuitry, including a DC power supply, energizes the coil when the microtome is moving the specimen holder downward a past a cutting knife. On the upward stroke of the cutting knife, the coil is de-energized, and the spring pushes the specimen holder away from the knife so as to avoid any possibility of deleterious scrubbing, etc.

Figure 1:
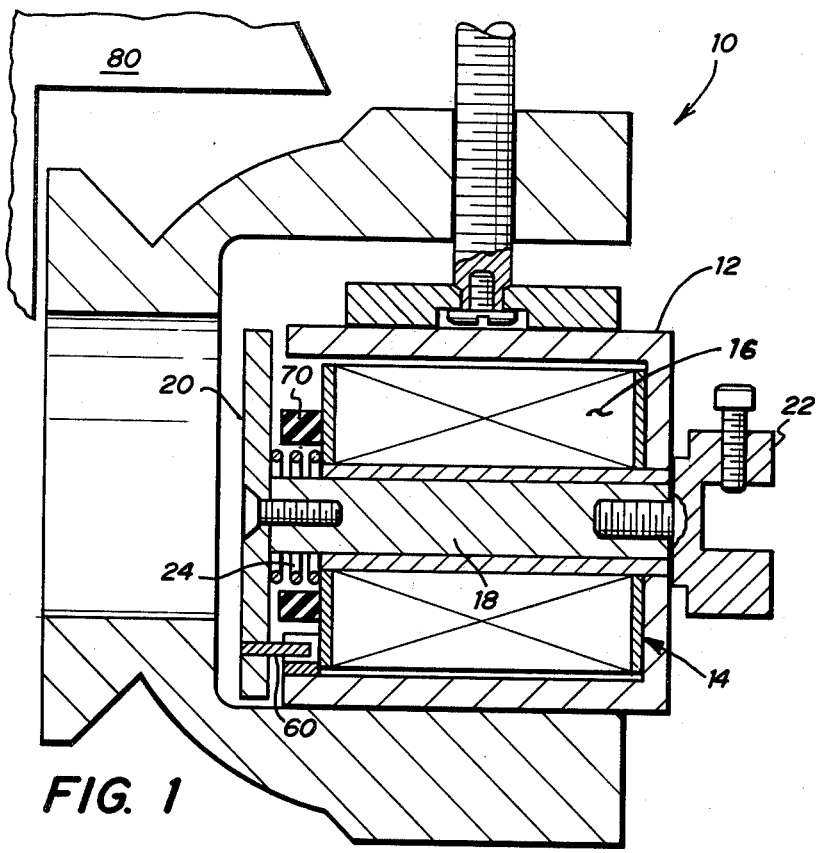
FIG. 1 is a cross-sectional, elevation view of one embodiment of the invention which is adapted to fit in the distal end of a cantilevered microtome arm which is configured to accept a standard ball.

Referring initially to FIG. 1 the apparatus 10 is shown in association with a very basic rotary microtome, i.e., one without any built in retracting mechanism. Exemplary of such microtomes are those which are commercially available from American Optical Corporation and sold under the trademark AO 820. The apparatus 10 includes a frame 12 having an external configuration which is adapted to be selectively fixed to the cantilevered arm which moves up and down in response to some reciprocating mechanism. If the frame 12 is small enough, it may fit within the space which traditionally receives a small wooden block upon which a paraffin-embedded specimen is mounted. Alternatively, the frame 12 may be larger than the traditional wooden block, and may be inserted in a housing which replaces the original ball that fits in the chuck of a conventional microtome.

Mounted within the frame 12 is a solenoid 14 which includes a coil 16 and movable core 18. The movable core 18 is preferably inserted with a slip fit in a hole that has been drilled in a soft iron core of a conventional solenoid. Clearance between the movable core and the drilled hole is preferably on the order of 0.0002 inch, such that a rigid support for the movable core is assured. Attached to that end of the movable core which is closer to the microtome (and which will be referred to as the rearward end) is a plate 20 having a size approximately the same as the envelope defined by the two legs of the U-shaped frame 12. In one practical embodiment of the invention, said plate has a rectangular cross section which is about one inch by one and one-quarter inch. Selectively fixed to the other (forward) end of the movable core is an auxiliary specimen holder 22. Preferably, the connection between the core 18 and the specimen holder 22 is through cooperating threads, in order that a first auxiliary specimen holder may be selectively removed and replaced with a second specimen holder.

A spring 24 is mounted within the frame and captured between the plate 20 and the end of the coil-supporting structure. Even in its rest position (as shown in FIG. 1), the spring 24 is slightly compressed so that it constantly urges the plate 20 and the movable core 18 rearwardly, i.e., away from the coil. The spring preferably has a spring constant of about 5,250 grams/cm, such that a force of about 525 grams can compress the spring by a distance of about one millimeter. Such a distance will likely be all that is necessary in order to insure separation of a specimen and the cutting knife during a return stroke.

With regard to the coil 16, it preferably has sufficient turns (e.g., about 4800 turns of No. 35 wire) to hold the movable core firmly against the frame 12 with a force of at least five pounds. That is, when the coil is energized and the plate 20 has become locked in static contact with the frame 12, the core 18 should ideally be held with a force of at least five pounds—to insure a firm support for the specimen and to obviate any possible chatter during sectioning. The need for such stability can perhaps be better appreciated when one remembers that it is common in modern laboratory practice to strive for tissue sections having thikness within the range of about 1–10 microns. If a plastic-embedded specimen was not firmly held during the cutting stroke, such very thin sections could never be reliably and repeatedly obtained. With a coil 16 having about 32 ampere turns, the movable core 18 can be held in its forward position with a force of about eight pounds—which has been found to provide highly satisfactory results, and may be considered to be the preferred embodiment of the invention.

Also provided as a part of the apparatus 10 is appropriate electrical circuitry for energizing the coil 16 when the microtome is moving the specimen holder downward past a cutting knife. The electrical circuitry preferably includes a transformer 30 for converting readily available 110 volt power to about 30 volts, which is then rectified to DC through the full wave rectifier 32. The output of rectifier 32 is then filtered with a RC network 34 to produce a filtered 30-volt DC power supply for the coil 16. The transformer 30, the full-wave rectifier 32 and the RC filter 34 may be conveniently housed in a small box 31 in order to foster portability, etc. And, connection between the power supply box 31 and the rest of the electrical circuit is advantageously accomplished with jack-type connections, so that the various parts of the system may be easily handled, connected, disconnected, etc.

Figure 3:
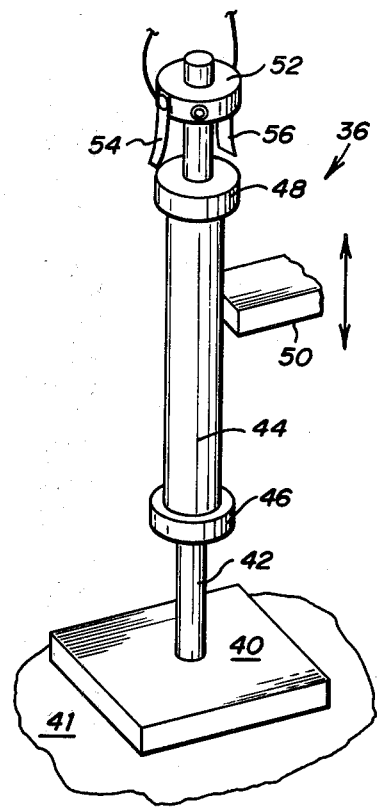
FIG. 3 is a perspective view of one embodiment of a slide switch which may be used to control energization of the solenoid.
Figure 2:
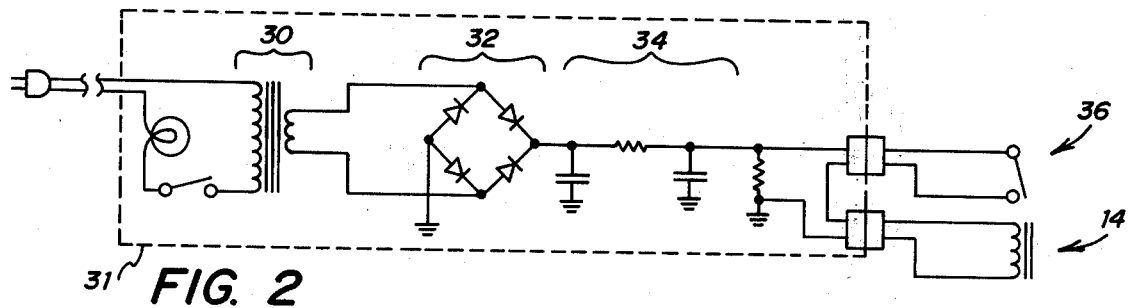
FIG. 2 is a diagram of the electrical circuitry for periodically energizing the solenoid of the invention.

An acutating switch 36, which sequentially energizes and de-energizes the coil 16, is preferably attached to the microtome housing in such a way as to be actuated by the standard reciprocating motion of the microtome. One way in which this is advantgeously accomplished is shown in FIG. 3, wherein a base 40 is affixed with an adhesive or the like to the floor 41 of the microtome housing. Extending upwardly from the base 40 is a post 42 which carries a slider 44 having protruding flanges 46, 48. The base 40 is positioned with respect to the microtome housing in such a way that a tripper arm 50 affixed to the microtome reciprocating mechanism (not shown) bears against the lower part of flange 48 when the tripper arm is rising, and against the upper part of flange 46 when the tripper arm is falling. The reason for preferring a mechanism of this type which includes the widely spaced flanges 46, 48 on slider 44 is that the reciprocating mechanism of a commercially available unit will commonly travel about 1¾ inch in making one full excursion. And, such a lengthy distance is certainly not necessary in order to make and break contact in the switch 36. Hence, the construction shown in FIG. 3 serves as a travel reducing mechanism for the moving part of the switch.

A further advantage of the construction shown in FIG. 3 is that it has built-in adjusting features which permit this apparatus 10 to be utilized on microtomes manufactured by various companies. That is, by adjusting the position of insulator block 52 with respect to post 42, the elevation at which flange 48 makes contact with contact arms 54, 56 may be varied. However, it should be understood that the manner of sequentially energizing the coil 16 might be varied as necessary to fit the particular physical constraints of a given microtome; and, it would be entirely feasible to utilize a microswitch which is tripped by the rotary crank as the technician manually turns said crank. Hence, the exact manner of energizing the electrical circuitry is a matter of at least some choice.

Figure 4:
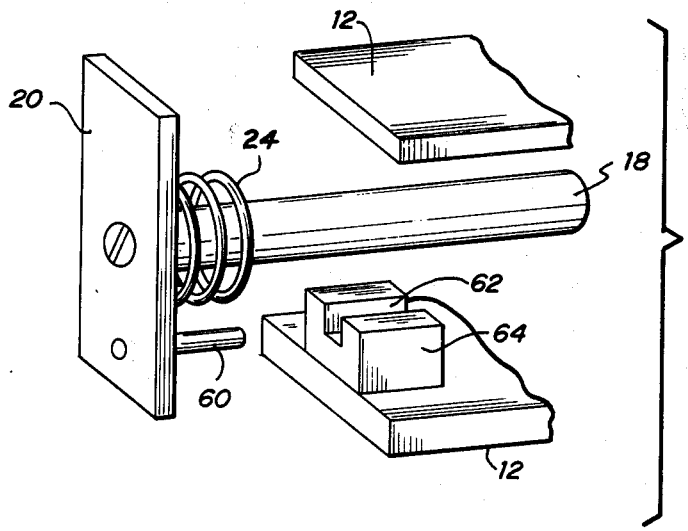
FIG. 4 is a partially exploded and schematic view of the fixed frame and movable core which are parts of the solenoid.

In order to foster excellent control of the tissue block, it is preferred that the movable core 18 be restrained against rotation about its longitudinal axis. One way in which this is done is through use of a pin 60 (FIG. 4) which is rigidly fixed to the frame 20, extending in the direction of travel of the core 18 as it makes its excursions. A groove 62 in block 64 receives the pin 60 with a reasonably snug fit, so as to inhibit rotation of the movable core 18 about its longitudinal axis.

When the coil 16 is initially energized, the soft iron plate 20 and core 18 will be rapidly drawn toward the coil, and it would be entirely possible to accelerate the plate and core with such a force as to contribute to at least some vibration when the plate 20 strikes the U-shaped housing 12. To inhibit the introduction of any vibration into the specimen-holding system, a damping means such as an annular body of resilient material 70 is preferably positioned between the plate 20 and the coil end—for cushioning the plate as it approaches the frame 12 as a result of attraction by the established magnetic field. Such a resilient damping medium 70 may be made of a material such a neoprene rubber and the like, having a size and hardness such that it can be fully compressed by the coil acting on the movable core. That is, during the downward stroke of the work-holding chuck 80, it is important that there be no resiliency in the system; on other words, for repetitive and reliable slicing of tissue sections, there should be rigid metal-to-metal contact in all parts of the system. And, while some damping of plate 20 is desirable to preclude bouncing and the like, such damping must not interfere with the accuracy of the sectioning process.

In installation of the invention, a technician would typically lift the cover of a conventional rotary microtome to expose the up/down reciprocating mechanism. A switching device, such as that shown in FIG. 3, would then be positioned in such a way that a tripper arm 50, may make and break the switch 36 at appropriate extremes of arm movement. As a practical matter, the tripper 50 may even be one of the existing retaining screws for the reciprocating slide. The base 40 may then be glued to the floor 41 of the microtome housing. The insulator block 52 may be moved up or down as required in order to achieve a precise current interruption for the solenoid 14. Next, the frame 12 and its enclosed solenoid 41 would be inserted into the space previously reserved for specimen blocks, with the auxiliary specimen holder 22 being at the front of the microtome. When the two jacks are connected to the power supply box 31 and the on/off switch is actuated, the system is immediately operational. The combination of the basic microtome and the apparatus 10 is then functionally as effective as the more complicated (and expensive) microtomes shown in U.S. Pat. Nos. 3,077,806 to Hellstrom and 3,771,405 to Blum.

At any time that a technician wishes to change a specimen holder 22, he may do so by merely unscrewing the first holder and replacing it with another holder. In this manner, a paraffin specimen holder may be readily removed and a holder designed to optimally hold a glycol methacrylate embedment can be quickly substituted.

In operation, the reciprocating and indexing mechanism of the microtome will function exactly as it did when it came from the factory. That is, it will travel up and down as a technician turns the exterior crank on the microtome, and it will index forward at the end of each upward stroke. At about the time the microtome chuck 80 reaches the top end of its excursion path, the flange 48 will make electrical contact with the arms 54, 56, thereby energizing the coil 16--which forces the plate 20 forward until it is halted by frame 12. The coil 16 will remain energized as long as the microtome chuck is moving downward, because there is no interruption of current to the coil. However, as the tripper 50 nears the bottom of its excursion path, it bears against flange 46 and pushes slider 44 downward by an amount sufficient to break electrical contact between flange 48 and the two contact arms 54, 56. The coil 16 will thereupon be de-energized, and the spring 24 will act to urge the plate 20 and the attached specimen holder 22 to the rear. The specimen holder 22 remains at the rear while the microtome arm is returning to the top of its excursion path. Eventually, tripper 50 will again make contact with flange 48, energizing the coil 16 and preparing the specimen for a new downward stroke past the knife. This sequence is repeated indefinitely as long as the crank is rotated.

If an occasion ever arises when it would be desirable to transfer the apparatus 10 to a different microtome, this can be readily accomplished by simply removing the frame 12 and any attendant structure from the chuck 80. Since the microtome has not been really altered with regard to its operation, then it is immediately in condition to be used in the manner that the original manufacturer anticipated. That is, no permanent alterations were required when the apparatus 10 was installed, and none are required when it is removed. However, if the glue which was used to affix the switch assembly 36 happened to be permanent glue, then it may be necessary to have several such switch assemblies—with one assembly being permanently connected to each microtome in which the retracting apparatus is to be utilized. Then, when a technician wishes to switch from one microtome to another, he simply places the frame 12 in the microtome chuck and connects the wire which leads from the actuating switch 36 to the power supply.

Another advantage of the switch assembly 36 shown in FIG. 3 is the control that is provides in adjusting the respective times at which a specimen holder is alternately advanced and retracted. That is, by adjusting the times at which the solenoid 14 is energized and de-energized, it is possible to insure that the specimen is properly positioned with respect to the cutting knife before the microtome arm ever starts its vertical excursions. In this way the possibility of any chatter or vibration as a result of in and out movement of the specimen holder is essentially obviated. Also, the judicious selection of a power source contributes to the stability of the specimen holder as it makes its downward excursion. A filtered source of power is preferred in order to eliminate the possibility of imparting any 60-cycle mechanical vibrations into the specimen holder—as a result of a 60-cycle fluctuation in the energizing current flowing through the coil.

In addition to the specific embodiments disclosed herein, it should be apparent to those skilled in the art that modifications thereof can be made without deviating from the basic invention. For example, the preferred form of the invention involves moving the specimen holder toward a cutting position with an energized coil, and moving it backward away from the knife with some other source of energy (such as a compressed spring). But, it would be entirely appropriate to reverse this arrangement—as long as sufficient rigidity is insured for the specimen holder in its forward position. Similarly, in the embodiment disclosed herein it is preferred that the specimen holder be held against a mechanical stop with an electromagnetic force that is several times greater than an opposing force tending to move the speciment back to a retracted position. However, if it should be desired to increase the retracting force to much above one pound, then the relative sizes of the pushing and pulling forces might be made more nearly equal. It should be understood, therefore, that these and other modifications could be made by those skilled in the art without departing from the spirit of the invention described herein.

What is claimed is:

1. An apparatus for selective attachment to a rotary microtome in order to permit separation of the specimen from a cutting knife during the return stroke of the specimen, comprising:
   (a) a frame having an external configuration which is adapted to be selectively fixed to the reciprocating mechanism of a rotary microtome;
   (b) a solenoid mounted within said frame, said solenoid including a coil, a movable core, a plate fixed to one end of said movable core, and an auxiliary speciment holder fixed to the other end of the movable core;

(c) a spring mounted within the frame so as to constantly urge the plate and the movable core rearwardly away from the coil; and (d) means including a power supply and electrical circuitry for energizing said coil when the microtome is moving the specimen holder downward past a cutting knife, and for de-energizing said coil when the microtome is moving the specimen holder upward in preparation for a subsequent cutting stroke, whereby said spring acts to retract the auxiliary specimen holder during the upward movement of said specimen holder.

2. The apparatus as claimed in claim 1 wherein the frame is fixed to the reciprocating mechanism by mounting it on the specimen chuck holder of the microtome.

3. The apparatus as claimed in claim 1 and further including means for restraining the movable core against rotation about its longitudinal axis.

4. The apparatus as claimed in claim 1 and further including damping means positioned below the plate for cushioning the plate as it approaches the frame in response to a magnetic field established by said solenoid.

5. The apparatus as claimed in claim 1 wherein the electrical circuitry includes a limit switch which is attached to a microtome housing in such a way as to be actuated by the reciprocating mechanism of the microtome.

6. The apparatus as claimed in claim 1 wherein the power supply constitutes a filtered DC power supply having an output of about 30 volts.

7. The apparatus as claimed in claim 1 wherein the front end of the movable core includes threads that permit a first auxiliary specimen holder to be removed and replaced with a second specimen holder.

8. The apparatus as claimed in claim 1 wherein the excursion length of the movable core as the coil is sequentially energized and de-energized is about one millimeter.

9. The apparatus as claimed in claim 1 wherein a solenoid is connected to the power supply through exposed wires having jack-type connectors, whereby the apparatus may be easily removed from the microtome and the solenoid disconnected from the power supply.

10. The apparatus as claimed in claim 1 wherein the solenoid is sized so as to hold the movable core static in its forward position with a force of at least 5 pounds when the coil is energized.

11. The apparatus as claimed in claim 1 wherein the solenoid is sized so as to hold the movable core static in its forward position with a force of about 8 pounds when the coil is energized.

12. The apparatus as claimed in claim 1 wherein the spring is a coil spring having a spring constant of about 5,250 grams/cm.

13. The apparatus as claimed in claim 1 wherein the movable core slides within a drilled hole in an iron core in said solenoid, and the clearance between said core and the drilled hole is on the order of 0.0002 inch, whereby a slip fit is realized and a rigid support for the specimen is assured.

14. The apparatus as claimed in claim 1 wherein the electrical circuitry includes a switch which effectively controls forward and backward movement of the specimen holder, and wherein the actuation position of said switch is adjustable with respect to the vertical excursion path of the microtome arm.

15. The apparatus as claimed in claim 1 wherein the apparatus is packaged in several discrete units, all of which may be selectively connected to and removed from the microtome without affecting any major adjustment or basic operation of the original microtome.

16. The method of achieving selective separation between a specimen holder and a cutting knife which is affixed to the static frame of a microtome, comprising the steps of:

(a) mounting said specimen holder on a movable core of a solenoid; and (b) alternately energizing and de-energizing the solenoid in order to alternately advance the specimen holder toward and retract it from the static cutting knife, with said specimen holder generally being in a forward position during a downstroke past the cutting knife and generally being in a retracted position during an upstroke adjacent the cutting knife.

17. The method as claimed in claim 16 wherein a spring biases the specimen holder to the rear at all times, and the solenoid advances the specimen holder toward the cutting knife in opposition to said spring when the solenoid is energized.

18. The method as claimed in claim 16 wherein the specimen holder is advanced to its forward position by solenoid just before it starts its downward stroke past the cutting knife, and the holder remains in its forward position during substantially the entire downward stroke.

19. The method as claimed in claim 16 wherein the specimen holder is advanced against a mechanical stop prior to being translated downward with respect to the fixed knife, and said holder is held against said mechanical stop by the passage of current through the solenoid during said downward translation.

20. The method as claimed in claim 19 wherein the holder is held against the mechanical stop by passage of a filtered DC current through the solenoid.

21. The method as claimed in claim 19 wherein the specimen holder is held against the mechanical stop by force of about eight pounds during such time as the holder translates downward past the fixed knife.

22. The method as claimed in claim 19 wherein the specimen holder is held against the mechanical stop by an electromagnetic force which is several times greater than an opposite force tending to move the specimen holder to a retracted position, such that the holder is very stable in its forward position.

* * * * *